United States Patent [19]

Eskamani et al.

[11] Patent Number: 4,536,584
[45] Date of Patent: Aug. 20, 1985

[54] PROCESS FOR THE THERMOCHEMICAL CONVERSION OF BIOMASS

[75] Inventors: Abolghassem Eskamani, Aurora; Warren H. Krause, Cleveland, both of Ohio

[73] Assignee: The Standard Oil Company (Ohio), Cleveland, Ohio

[21] Appl. No.: 538,245

[22] Filed: Oct. 3, 1983

[51] Int. Cl.$^3$ .................. C07C 31/00; C07C 45/00
[52] U.S. Cl. .................. 549/429; 549/483; 549/507; 549/508; 549/509; 562/513; 568/338; 568/383; 568/449; 568/679; 568/840
[58] Field of Search .......... 549/429, 483, 507, 508, 549/509; 562/513; 568/338, 383, 449, 679, 840

[56] References Cited

U.S. PATENT DOCUMENTS

| | | | |
|---|---|---|---|
| 2,535,060 | 12/1950 | Gresham | 260/449 |
| 2,551,579 | 5/1951 | Berl | 260/125 |
| 3,505,204 | 4/1970 | Hoffman | 208/10 |
| 3,714,038 | 1/1973 | Marsh | 210/59 |
| 3,828,077 | 8/1974 | Nowack et al. | 549/507 |
| 3,864,097 | 2/1975 | Urban | 44/50 |
| 4,009,219 | 2/1977 | Tamers | 260/673 |
| 4,300,009 | 11/1981 | Haag et al. | 585/408 |
| 4,313,011 | 1/1982 | Weil | 585/240 |
| 4,459,419 | 7/1984 | Seemuth | 549/429 |

OTHER PUBLICATIONS

Jones, Chemical Engineering, (1978, Jan. 2) pp. 87–94.

Primary Examiner—Richard L. Raymond
Attorney, Agent, or Firm—T. P. Schur; J. G. Curatolo; L. W. Evans

[57] ABSTRACT

A process is provided for the thermochemical conversion of biomass to useful gaseous and liquid organic products. The inventive process utilizes a catalyst to obtain increased yields of gaseous and liquid organic products and decreased yields, if any, of solid and semi-solid tar/oils.

10 Claims, No Drawings 4,536,584

PROCESS FOR THE THERMOCHEMICAL CONVERSION OF BIOMASS

BACKGROUND OF THE INVENTION

This invention relates to a process utilizing novel catalysts for the conversion of biomass to useful gaseous and liquid organic products. More specifically, the invention relates to a process whereby biomass is converted substantially to useful gaseous and liquid organic products in the presence of ruthenium-bearing catalysts.

An awareness of the limitations of petroleum reserves has caused an increased interest in finding alternative energy sources. Renewable energy sources, such as crops which can be grown and processed to supply chemical and energy demands, are particularly attractive. Chemical and energy yields vary from crop to crop depending on the chemical constituency of each plant. Compositions vary from wood which is about all lignocellulosic to some perennial crops, such as milkweed (asclepias), which naturally contain up to about 43 weight percent based on the total weight of the plant of useful recoverable organic compounds. Other plant sources in which useful recoverable organic compounds comprise a portion of their compositions include, but are not limited to, plants belonging to the families of Euphorbiaceae, Moraceae, Apocynaceae, Asclepiadaceae and Compositae. Specific genera that contain recoverable hydrocarbons as a portion of their compositions include Hevaea, Manihot, Mabea, Sabium, Ricinus, Asclepias (milkweed), Solidago (goldenrod) and Euphorbia. E. lathrus (gopher plant) and E. tirucalli (aveloz, milk bush) are also plants that generate hydrocarbon constituents. Other examples include E. resinifera, E. trigona, E. cerifera (candelilla) and Parthenium argentatum (guayule).

Generally, three classes of products are obtained from the thermochemical conversion of biomass: gaseous products such as carbon dioxide, hydrogen, methane, and other light hydrocarbons; liquid organic compounds which are usually water-soluble as well as soluble in an organic solvent like acetone, methyl ethyl ketone and alcohols, such as alcohols, ketones and phenols, referred to hereinafter as liquid organic products; and a solid or near solid product which comprises tar/oils and char.

Heavy tar/oils are the chief product of most thermochemical conversions of biomass. Such tar/oils are usually solid or near solid at room temperature and difficult to handle and utilize. These tar/oils are used principally as second-grade fuel material and are valued on the basis of their heating values, measured in BTU/lb. Tar/oils typically have heating values in the range of from about 10,000 BTU/lb to about 16,000 BTU/lb.

The gaseous and liquid products from the thermoconversion reaction of biomass may be used directly as heating fuels or have other direct applications or be used as intermediates for the synthesis of other chemicals. Much attention in the field of thermochemical conversion of biomass has been directed toward the decreased production of solid and semisolid tar/oils and the increased production of gaseous and liquid organic products, predominantly gaseous and liquid hydrocarbons. U.S. Pat. No 2,551,579 to Berl discloses a process for the production of liquid or semiliquid organic compounds from plant material. Berl's process comprises heating plant matter containing carbohydrates and lignin in a closed system to a temperature between 150° C. and 370° C. in the presence of water and an alkaline-reacting ammonium compound such as ammonium sulfide or ammonium hydrosulfide.

U.S. Pat. No 3,505,204 to Hoffman describes a process for the direct conversion of carbonaceous material to hydrocarbons. This is a catalytic conversion of materials such as coal to oxygen-containing organic materials such as alcohols aldehydes, ketones, and acids. The catalyst is a two-component system comprising an alkali metal or alkaline earth metal compound and a Group VIII transition metal oxide. The carbonaceous material, steam and catalyst are reacted at a temperature between about 220° F. and 280° F. The handling, processing, and products obtained from biomass conversion are quite different from those obtained from the conversion of coal. Thus, the process disclosed by Hoffman would not be considered directly applicable to biomass conversion nor would any hydrogenation catalysts be expected to perform similarly when contacted with coal products and biomass material.

What is lacking in the field of thermochemical biomass conversion is a process which converts biomass into useful materials substantially other than tar/oils.

Therefore, it is one object of this invention to provide a process for the direct thermochemical conversion of biomass to predominantly gaseous and liquid organic products.

It is another object of this invention to provide a novel catalyst for the selective conversion of biomass to gaseous and liquid organic compounds.

These and other objects of the invention, together with the advantages thereof, will become apparent from the following specification and appended claims:

SUMMARY OF THE INVENTION

The present invention relates to a process for the thermochemical conversion of biomass having a conversion rate of at least 90 percent and wherein at least 3 percent of the converted biomass, based on the total weight of the biomass, are liquid organic compounds, which process comprises contacting the biomass with a ruthenium-bearing catalyst under reducing conditions and at a temperature of at least 100° C. and at a pressure of at least 20 atmospheres.

DETAILED DESCRIPTION OF THE INVENTION

The process for converting biomass to organic products in accordance with the present invention is a thermochemical process. The biomass material may be any plant substance. Preferably, the biomass is derived from plant material having a significant amount of useful recoverable organic compounds, such as milkweed (asclepias).

The biomass material to be converted may be provided in any form such as chunks, chips or dust. Preferably, the biomass is ground into a powder and disposed in an aqueous solution. The biomass may comprise raw plant material or preprocessed biomass material such as biomass material that has already undergone an extraction process. Biomass from crops such as milkweed and jojoba which contain a significant amount of hydrocarbons may be extracted with suitable solvents such as acetone, benzene, petroleum solvents and the like to remove an initial hydrocarbon portion of the fraction of the biomass. As an example, milkweed may be extracted with hexane to yield a liquid hydrocarbon material comprising latex, phenols and waxes and an extractive residue comprising proteins and carbohydrates. The extractive residue comprises about 91 percent of the original biomass of which at least 3 and up to about 45 percent may be recovered as liquid organic products.

In accordance with this invention, the biomass material, either whole or extracted or both, is placed in a solution in contact with a ruthenium-bearing catalyst and subjected to elevated temperatures and pressures under a reducing atmosphere in a batch or continuous process reactor. Any suitable solvent which does not interfere with the effectiveness of the catalyst may be used in the biomass solution. Examples of such solvents include water, creosote, and high boiling point alcohols and other organic solvents. Preferably, the solvent is water and the biomass is accordingly disposed in an aqueous solution.

In accordance with this invention, a significant portion of the biomass is converted via a thermochemical reaction to water soluble $C_1$–$C_5$ alcohols, aldehydes and ketones. It has unexpectedly been found that ruthenium-bearing catalysts under reducing conditions produce a significantly smaller tar/oil fraction and a significantly larger water soluble organic fraction than has been obtained by other thermochemical biomass conversion catalysts and processes. Examples of ruthenium-bearing catalysts include the metal; ruthenium oxides such as ruthenium dioxide, ruthenium sesquioxide, ruthenium tetroxide and ruthenium pentoxide; ruthenium carbonyls such as diruthenium monacarbonyl and ruthenium carbonyl hydride; ruthenium salts of organic carboxylic acids and other ruthenium-bearing compounds. Preferred ruthenium-bearing catalysts include the ruthenium oxides. Most preferred is ruthenium dioxide. When the ruthenium-bearing catalyst is a ruthenium oxide, the catalyst may be reduced during the thermochemical conversion process under the reducing conditions of the process.

The catalyst may be homogenous or heterogenous, that is, it may be suspended in the biomass-containing solution or may be fixed as on a high surface area fixed bed of zeolite, diatomaceous earth, clay, charcoal, silica gel or silicon carbide, or otherwise disposed in a heated reaction chamber. The ruthenium-bearing catalyst may, for example, be disposed as particles stirred in the biomass solution or may be provided as a coating on carrier particles, or may be deposited on a fixed bed submerged in the biomass solution. The weight ratio of catalyst to biomass may range from about 1:100 to about 1:1 or less. Preferably, the ratio of catalyst to biomass is between about 1:1 and about 1:20. More preferably, the ratio of catalyst to biomass is about 1:10. The process by which biomass is converted to gaseous and liquid organic products in accordance with the instant invention may be amenable to use in a batch or continuous process.

The weight ratio of biomass to solvent does not effect the inventive process and for practical applications may be from about 1:0.5 to about 1:100. More preferably, the weight ratio of biomass ranges from about 1:5 to about 1:10, and optimally from about 1:8 to about 1:10.

The reaction will proceed at temperatures that are maintained at least at about 100° C.; the reaction does not proceed to a substantial degree at temperatures below 100° C. Preferably, the biomass-containing solution is maintained at a reaction temperature of between about 275° C. and about 320° C.

The reaction proceeds at a suitable rate under pressures of at least about 20 atmospheres. Preferably, the reactor is pressurized to about 68 atmospheres or more. It is also preferred to purge the reactor with an inert gas such as nitrogen or argon prior to introducing a pressurizing gas so as to remove about all of the oxidative gases that may be in the reactor. The reactor is then preferably pressurized with a reducing gas. Hydrogen, carbon monoxide and mixtures thereof are preferred reducing gases for pressurizing the reactor vessel. It has been observed that increased amounts of alcohols are formed from biomass when the thermochemical conversion reaction takes place predominantly under high pressures and high temperatures.

The process in accordance with this invention proceeds favorably when the biomass-containing solution remains under elevated temperatures and pressures and in the presence of a ruthenium-containing catalyst for a period of time of from about 10 minutes to about 120 minutes. Preferably, the reaction proceeds for from about 20 minutes to about 90 minutes. Optimally, the thermochemical conversion of biomass in accordance with the present invention proceeds for about 45 minutes. Whereas most catalysts convert biomass material predominantly to tar/oils which are solid at room temperature, and only soluble in organic solvents, it has been surprisingly found that ruthenium and ruthenium-bearing catalysts, either reduced or utilized in a reducing atmosphere, unexpectedly convert biomass via a thermochemical reaction to predominantly $C_1$–$C_5$ alcohols, aldehydes, and ketones and any tar/oils formed are liquid at room temperature and soluble in water. Additionally, process variables may be adjusted so that the amount of gaseous and liquid organic compounds produced is increased while the yield of liquid tar/oils is reduced. Lower ratios of catalyst to biomass significantly reduce the formation of tar/oils from the thermal conversion of biomass.

When milkweed is utilized as the biomass source for conversion in accordance with this invention, a water-soluble fraction is obtained that comprises methanol, ethanol, acetone, pentanone, propanol, 2-methyl propanol, cyclopentanone, cyclohexanone, 3-methyl butanol, cycloheptanone, cyclopentanol, acetic acid, tetrahydrofuran and dihydrofuranone. When cellulose is used as the biomass source it is converted in accordance with this invention to provide a water-soluble fraction that includes 2-propanone, 2-propanol, tetrahydrofuran, 2-butanone, 2-butanol, 2-pentanone, 2-pentanol, 2-hexanone, cyclopentanone, cyclohexanone, cyclopentanol, acetic acid, propionic acid, 2,5-hexanedione, butanoic acid, dihydromethylfuranone, pentanoic acid, cyclohexanone, $C_5H_8O_3$ and $(C_2H_5O)_2CH_2$.

EXAMPLES

The following examples are presented to more thoroughly illustrate the present invention and are not intended in any way to be limitative thereof.

Each of the following examples involved thermochemically reacting a biomass-containing solution having a conversion catalyst therein, except Examples 1, 7 and 8 presented as control examples wherein no catalyst was present in the biomass-containing solution.

The reactions took place in a 300 ml. Parr bomb reactor. The vessel was constructed of Hastelloy B and rated for a maximum working pressure of 137 atmospheres at 350° C. Unless otherwise stated, the biomass feedstock comprised whole plant milkweed which had been ground into a fine powder and dried in an oven at about 100° C. to remove its water content.

In each of the examples, about 10 gms of biomass was mixed into about 50 ml. of distilled water. Except for the non-catalyzed control examples, a measured amount of catalyst, provided as a fine powder, was then disposed in the biomass-containing solution to form an activated solution.

The activated solution was placed in the reactor and the reactor purged with nitrogen. The reactor was then pressurized to a desired pressure with hydrogen gas and heated to a designated temperature. The activated solution was stirred during a heated, pressurized reaction period, then a gas sample was taken and the solution cooled and vented to return the reacted solution to room temperature and atmospheric pressure.

The aqueous solution was poured through a milipore filter and analyzed for organic products. The remaining material in the reactor was removed with acetone and passed through the milipore filter. The acetone-soluble materials were recovered by evaporating the acetone.

nor any of the Examples using catalysts similar in structure to ruthenium dioxide yielded more than 88 weight percent conversion of biomass. The percent of biomass converted to aqueous-soluble organic products was 3.77 percent in the uncatalyzed Example 1 and less than that in Examples 2–5 which utilized compounds having crystal structures similar to ruthenium dioxide. Whereas the example in which ruthenium dioxide was present produced no solid/semisolid tar/oils, the uncatalyzed example contained about 16.5 weight percent tar/oils after biomass conversion and Examples 2–5 yielded from about 18.8 to about 25.0 percent tar/oils after biomass conversion. This high catalytic activity of the ruthenium-bearing catalyst of Example 6 was obtained at a catalyst concentration that was half of the catalyst concentration used in Examples 2–5. Thus, the ruthenium-containing catalyst is unique for its capability to convert biomass and the selective production of liquid organic compounds from biomass.

TABLE 1

BIOMASS CONVERSION WITH VARIOUS CATALYSTS

| Example | Catalyst | Catalyst to Biomass Ratio | Weight Percent Conversion | Total Organic Carbon in Water-Soluble Fraction | Weight Percent Converted to Water-Soluble Organics | Weight Percent Converted to Tar/Oils | Heating Valve of Tar/Oils Fraction (BTU/lb.) |
|---|---|---|---|---|---|---|---|
| 1 | None | — | 85 | 1.99 | 3.77 | 16.5 | 15,400 |
| 2 | $S_nO_2$ | 1:10 | 83.7 | 2.15 | 1.21 | 18.8 | 15,293 |
| 3 | $GeO_2$ | 1:10 | 88.0 | 1.62 | 1.79 | 20.0 | 17,000 |
| 4 | $TiO_2$ | 1:10 | 84.5 | 1.70 | 3.41 | 25.0 | 12,574 |
| 5 | $V_2O_4$ | 1:10 | 84.3 | 1.88 | 3.56 | 24.5 | 14,442 |
| 6 | $RuO_2$ | 1:20 | 100.0 | 3.33 | 15.05 | 0 | — |

These acetone-soluble materials were tar/oils. The residue left in the milipore filter comprised catalyst and non converted biomass referred to as char. The char was used to calculate the percent conversion of biomass.

The following data were recorded:
total weight percent of biomass converted;
total organic carbon (TOC) in the water-soluble organic fraction;
weight percent of biomass converted to water-soluble alcohols and ketones;
weight percent of biomass converted to tar/oils, and heating value of formed tar/oils.

The filtered aqueous solution was analyzed via gas chromatography to identify five organic products; methanol, acetone, ethanol, isopropyl alcohol and n-pentanone.

EXAMPLES 1–6

These examples demonstrate the catalytic ability of a ruthenium-containing catalyst as compared to various other catalysts. Each of the reactions of Examples 1–6 was carried out at 300° C. and 68 atmospheres for a duration of 45 minutes. The ratio of catalyst-to-biomass in each example where catalyst was used was 1:10 except in Example 6 wherein the catalyst-to-biomass ratio was 1:20. No catalyst was used in the biomass conversion run of Example 1. Ruthenium dioxide was the catalyst used in Example 6. The catalysts of Examples 2–5 were commercially available oxide materials having similar crystal structures to ruthenium dioxide; $SnO_2$, $GeO_2$, $Ti_2$ and $V_2O_4$, respectively.

As can be seen from the data presented in Table 1, under the above-identified reaction conditions, ruthenium dioxide yields a 100 percent conversion of biomass producing no tar/oils and forming about 15 weight percent aqueous-soluble organic products. Under identical reaction conditions, neither the control Example

EXAMPLES 7–17

Biomass conversion reactions using a catalyst of ruthenium dioxide are presented in Examples 7–17 under various processing conditions. Temperature, pressure, catalyst-to-biomass ratio and duration of run were varied. Extractive-free residue of milkweed was used as the biomass feedstock. This was the residue left after the milkweed had been extracted with n-hexane. The extractive-free residue comprised about 91 weight percent of the original milkweed. The extractive-free residue was thoroughly dried in an oven and ground into a fine powder before being reacted in the manner described herein above.

In Examples 7 and 8, no ruthenium-containing catalyst was used so as to provide control runs.

The effects of reaction conditions on biomass conversion using a ruthenium dioxide catalyst are shown in Table 2. As can be seen from Table 2, the percent conversion of biomass in Examples 7 and 8 was 78 and 86.5 percent respectively. When a ruthenium-bearing catalyst was present, the percent conversion of biomass ranged from about 90 to 100 percent. Lower weight percent conversion of biomass was observed under conditions of low temperature, low pressure, high catalyst-to-biomass ratio and short duration of run. As can be seen by comparing Examples 9, 12 and 13, the catalyst-to-biomass ratio appears to have a significant effect on the percent conversion of biomass. The data support an inverse relationship wherein a lower catalyst-to-biomass ratio (1:10) corresponds to a greater percent conversion of biomass.

The tar/oils yield of these examples using a ruthenium dioxide catalyst ranged from zero percent to about 26.1 percent. More tar/oils were formed at high catalyst-to-biomass ratios (1:100). When the catalyst to

TABLE 2

EFFECTS OF REACTION CONDITIONS WITH RuO₂ CATALYST ON BIOMASS CONVERSION

| Example | Temp. (°C.) | Initial Pressure (atmospheres) | Catalyst to Biomass Ratio | Duration of Run (min.) | Weight Percent Conversion | Weight Percent Converted to Water-Soluble Organics | Weight Percent Converted to Tar/Oils | Tar/Oil Quality (BTU/lb) |
|---|---|---|---|---|---|---|---|---|
| 7 | 250 | 68 | None | 60 | 78 | 2.05 | 20.3 | — |
| 8 | 300 | 68 | None | 60 | 86.5 | 2.18 | 21.5 | — |
| 9 | 300 | 68 | 1:10 | 60 | 100 | 15.0 | 0 | — |
| 10 | 275 | 68 | 1:20 | 60 | 97.0 | 4.4 | 12.0 | 13,387 |
| 11 | 275 | 68 | 1:100 | 120 | 96.5 | 7.2 | 24.8 | 14,073 |
| 12 | 320 | 68 | 1:20 | 120 | 100.0 | 8.0 | 11.0 | 15,890 |
| 13 | 320 | 68 | 1:100 | 60 | 92.5 | 5.0 | 24.3 | 14,681 |
| 14 | 275 | 51 | 1:20 | 120 | 97.0 | 3.4 | 8.7 | 14,299 |
| 15 | 275 | 51 | 1:100 | 60 | 90.0 | 3.0 | 23.7 | 13,767 |
| 16 | 320 | 51 | 1:20 | 60 | 96.7 | 3.7 | 8.0 | 15,268 |
| 17 | 320 | 51 | 1:100 | 120 | 96.5 | 4.3 | 26.1 | 14,455 | biomass ratio was about 1:100, about 23.7 to 26.1 percent of the converted biomass comprised tar/oils. When the catalyst-to-biomass ratio was 1:20, about 8–12 percent tar/oils were produced. When the ruthenium-bearing catalyst was present at a catalyst-to-biomass ratio of 1:10, no tar/oils were formed. When no catalyst was used as in Examples 7 and 8, about 20–21.5 percent tar/oils were formed. Thus, lower catalyst-to-biomass ratios reduced the formation of tar/oils.

Since no tar/oils were formed when ruthenium dioxide was present at a catalyst-to-biomass ratio of 1:10, it appears that ruthenium dioxide may be catalyzing a reaction that competes with the reaction to form tar/oils. The reaction catalyzed by ruthenium dioxide may have occurred preferentially or tar/oils may have been formed which were then catalytically converted to other products by the ruthenium-containing catalyst.

EXAMPLES 18–19

The earlier-described reaction procedure was performed in a 500cc Parr rocking reactor to thermochemically convert sawdust. The rocking reactor was used to improve contact between catalyst particles and biomass. An aqueous solution of sawdust, which comprises primarily cellulose and lignin compounds, was reacted under conditions of 300° C. and 68 atmospheres of hydrogen for about 60 minutes. In Example 18 no catalyst was added to the biomass solution. A ruthenium-containing catalyst, ruthenium dioxide, was present in the biomass solution at a catalyst-to-biomass ratio of 1:10 in Example 19. Table 3 below lists the conversion data for these Examples.

When no catalyst was present, about 95 weight percent of the sawdust, based on the initial weight of the sawdust, was converted. About 85 volume percent of the gaseous products formed comprised hydrogen; less than about 1 percent of the gaseous products formed comprised methane. The water-soluble organic fraction had a total organic carbon (TOC) content of about 1.79 weight percent based on the total weight of the water-soluble fraction. About 36 percent of the converted biomass comprised tar/oils. When ruthenium dioxide was added to the biomass solution, 100 percent of the biomass material was thermochemically converted. The gaseous products formed by this conversion process comprised about 40 volume percent hydrogen and about 40 volume percent methane. The water-soluble organic fraction had a total organic carbon (TOC) content of about 2.61 percent. About 11 percent of the biomass material was converted to tar/oils.

TABLE 3

SAWDUST CONVERSION WITH RuO₂ CATALYST

| Example | 18 | 19 |
|---|---|---|
| Temperature (°C.) | 300 | 300 |
| Initial Pressure (atmospheres) | 68 | 68 |
| Solvent | water | water |
| Catalyst | none | RuO₂ |
| Catalyst-to-Biomass Ratio | none | 1:10 |
| Duration of Run (minutes) | 60 | 60 |
| Weight Percent Conversion | 95 | 100 |
| Total Organic Carbon in Water-Soluble Fraction | 1.79 | 2.61 |
| Volume Percent Methane in Gaseous Products | 0.69 | 40.1 |
| Weight Percent Biomass Converted to Tar/Oils | 36.25 | 11.65 |

Thus, Examples 1–19 demonstrate the catalytic ability of a ruthenium-containing catalyst to convert biomass, whether mostly cellulosic or of a widely varying composition such as milkweed, to significant portions of useful organic products and to reduce the formation of less-desired tar/oils products.

The selection of biomass material, solvents, ruthenium-containing catalysts, products derived from the thermochemical conversion of biomass utilizing a ruthenium-containing catalyst and reactant conditions can be determined from the preceding disclosure without departing from the spirit of the invention herein disclosed and described; the scope of the present invention including modifications and variations that fall within the scope of the appended claims.

We claim:

1. A process for the thermochemical conversion of plant-derived biomass having a conversion rate of at least 90 percent and wherein at least 3 percent of the converted biomass, based on the total weight of the biomass, are C1–C5 alcohols, aldehydes and ketones, which process comprises contacting said biomass with a ruthenium-bearing catalyst under reducing conditions at a temperature of at least 100° C. and at pressure of at least 40 atmospheres.

2. The process in accordance with claim 1 wherein said ruthenium-bearing catalyst is selected from the group consisting of ruthenium metal, ruthenium oxides, ruthenium carbonyls and ruthenium salts of organic compounds.

3. The process in accordance with claim 1 wherein said ruthenium-bearing catalyst is ruthenium dioxide.

4. The process in accordance with claim 1 wherein the ratio of ruthenium-bearing catalyst to plant-derived biomass is in the range of from about 1:1 to about 1:100.

5. The process in accordance with claim 1 wherein the ratio of ruthenium-bearing catalyst to plant-derived biomass is from about 1:1 to about 1:20.

6. The process in accordance with claim 1 wherein the ratio of ruthenium-bearing catalyst to plant-derived biomass is from about 1:1 to about 1:10.

7. The process in accordance with claim 1 wherein said conversion is carried out at a temperature of from about 275° C. to about 320° C.

8. The process in accordance with claim 1 wherein said conversion is carried out at a pressure of from about 20 atmospheres to about 68 atmospheres.

9. The process in accordance with claim 1 wherein said conversion is carried out at a pressure of about 68 atmospheres.

10. The process in accordance with claim 1 wherein said conversion occurs under a reducing atmosphere of hydrogen.

* * * * *